United States Patent [19]

Fischer et al.

[11] Patent Number: 4,748,126

[45] Date of Patent: * May 31, 1988

[54] PYRIDINE-FREE KARL-FISCHER REAGENT AND A PROCESS FOR THE DETERMINATION OF WATER THEREWITH

[75] Inventors: Wolfgang Fischer, Darmstadt; Karl-Dieter Krenn, Pfungstadt, both of Fed. Rep. of Germany

[73] Assignee: Riedel-de Haen AG, Seelze, Fed. Rep. of Germany

[ * ] Notice: The portion of the term of this patent subsequent to Apr. 5, 2000 has been disclaimed.

[21] Appl. No.: 245,405

[22] Filed: Mar. 19, 1981

[30] Foreign Application Priority Data

Mar. 19, 1980 [DE] Fed. Rep. of Germany ....... 3010436

[51] Int. Cl.$^4$ ............................................. G01N 33/18
[52] U.S. Cl. ........................................ 436/42; 204/1 T
[58] Field of Search ...................... 252/408; 23/230 R; 436/42; 116/206; 73/73, 76; 204/1 T

[56] References Cited

U.S. PATENT DOCUMENTS

| | | | |
|---|---|---|---|
| 2,780,601 | 2/1957 | Blomgren et al. | 436/42 |
| 2,967,155 | 1/1961 | Blomgren et al. | 252/408 |
| 3,656,907 | 4/1972 | Delmonte | 23/230 R |
| 3,661,797 | 5/1972 | Meloan et al. | 252/408 |
| 3,974,258 | 8/1976 | Poitevin et al. | 423/242 |
| 4,005,983 | 2/1977 | Dahms | 23/230 R |
| 4,146,454 | 3/1979 | Haber | 204/180.6 |
| 4,378,972 | 4/1983 | Scholz | 436/42 |
| 4,385,124 | 5/1983 | Verbeek et al. | 436/42 |
| 4,429,048 | 1/1984 | Scholz | 436/42 |

FOREIGN PATENT DOCUMENTS 3039511 5/1982 Fed. Rep. of Germany .
3008421 8/1982 Fed. Rep. of Germany .

OTHER PUBLICATIONS

Smith et al, J. Amer. Chem. Soc. 61, 2407 (1939). (1956).
Johansson, Anal. Chem. 28, 1166 (1956).

*Primary Examiner*—Barry S. Richman
*Assistant Examiner*—Robert J. Hill, Jr.
*Attorney, Agent, or Firm*—Millen & White

[57] ABSTRACT

A pyridine-free Karl-Fischer reagent for the determination of water which comprises (a) a solvent solution containing sulfur dioxide and an amine in a Karl-Fischer reagent solvent, the amine being functionally equivalent to pyridine in a Karl-Fischer reagent, and (b) a titrating agent containing iodine in a Karl-Fischer solvent; the molar ratio of amine to sulfur dioxide being about 2:1 to about 1:1 and the reagent being essentially free of pyridine.

14 Claims, No Drawings

PYRIDINE-FREE KARL-FISCHER REAGENT AND A PROCESS FOR THE DETERMINATION OF WATER THEREWITH

BACKGROUND OF THE INVENTION

The present invention relates to a pyridine-free Karl-Fischer reagent useful for the determination of water and also to a process for the determination of water using this reagent. Conventional reagents consist of a solvent solution for the sample to be examined and a titrating agent. The solvent solution contains sulfur dioxide and an amine, classically pyridine, in a solvent, and the titrating agent contains iodine in a solvent.

A number of suggestions for replacing pyridine in a Karl-Fischer reagent are known from the literature. In Anal. Chim. Acta, 94, 395 (1977), sodium acetate is used as a replacement for pyridine. However, this replacement is accompanied by certain disadvantages. For example, acetates are formed with the alcohol used as the solvent with water being released. Of course this water is troublesome in a method for the determination of water.

The use of amines in place of pyridine has also been described. See, for example, J. Amer. Chem. Soc., 61, 2,407 (1939). However, it was established that the stability of these solutions is very poor in comparison with pyridine-containing solutions. Furthermore, in the case of triethanolamine, the decomposition of the reagent, even in the manufacturing stage, can hardly be prevented.

Furthermore, in Anal. Chem., 28, 1,166 (1956), it has been established that no stable end points can be obtained on titration when pyridine is replaced by amines in such reagents. Thus, it appears from the state of the art that the replacement of pyridine by amines is not sensible because these reagents are either unstable or produce incorrect results.

SUMMARY OF THE INVENTION

Accordingly, it is an object of one aspect of this invention to provide a pyridine-free Karl-Fischer reagent which is stable and enables exact analytical results.

Upon further study of the specification and appended claims, further objects and advantages of this invention will become apparent to those skilled in the art.

These objects have been achieved by one aspect of this invention by providing a pyridine-free Karl-Fischer reagent for the determination of water which comprises a solvent solution containing sulfur dioxide and an amine in a solvent, and a titrating agent containing iodine in a solvent, wherein the molar ratio of amine to sulphur dioxide is about 2:1 to about 1:1, preferably about 1:1.

These objects have also been achieved by another aspect of this invention by providing a process for the determination of water using the pyridine-free Karl-Fischer reagent of this invention.

DETAILED DISCUSSION

In the conventional Karl-Fischer reagent, the pyridine is used in a threefold to fourfold molar excess relative to the sulfur dioxide. If this ratio is also retained for other basic components, unstable end points result during titration and the reagent cannot be used for volumetric determinations of water.

Surprisingly, it has been found by this invention that a stable Karl-Fischer reagent which produces exact end points can be obtained if the required particular molar ratio of amine to sulfur dioxide is used.

The pyridine-free Karl-Fischer reagent of this invention accordingly comprises two solutions, namely a solvent solution and a titrating agent. The solvent solution contains sulfur dioxide and amine in a solvent and is used to take up the sample, the water content of which is to be determined. The titrating agent is a solution of iodine in a solvent, which is adjusted to a constant titer.

Examples of suitable amines for use in the reagent of this invention include amines functionally equivalent to pyridine in the Karl-Fischer test, e.g., ethanolamine, diethanolamine, triethanolamine, morpholine, N-methylmorpholine, aniline, dimethylaniline, diethylamine, triethylamine, diisopropylamine, tri-n-butylamine, ethylenediamine, or diphenylamine and the like, preferably mono-, di- and tri-ethanolamine. Mixtures of such amines can also be used, as can other equivalent amines.

Suitable solvents for use in both the solvent solution and also in the titrating agent include all the solvents described for this purpose in the literature, preferably alcohols and/or glycols, in particular lower alcohols, e.g., of 1–6 C atoms, such as methanol, ethanol, propanol and the like, and also ethylene glycol and ethylene glycol mono-$C_3$-alkyl ethers. Such solvents can be used individually or in any desired mixing ratio. It is thus possible, for example, to dissolve the amine in an alcohol and the iodine in a glycol, or to dissolve both in any desired mixing ratio of alcohols, glycols or mixtures of both types of solvent.

With the pyridine-free Karl-Fischer reagent of this invention, the end point of the volumetric determination of water can be determined by a visual, photometric or electrometric method (dead-stop method or coulometric method). The reagent is suitable both for use in automatic titrating devices and also as a field method. The field method is only made possible because of the replacement of the conventional methanol by solvents of low vapor pressure.

The replacement of pyridine by amines produces a number of advantages. The change at the equivalence point is clearer than with the conventional Karl-Fischer reagents because the color change is from colorless to yellow instead of from yellow to brown. The reagent is less toxic and, overall, it causes less environmental pollution and is less expensive.

The titration is generally carried out with the exclusion of atmospheric moisture. In the visual titration, the criterion used is a color change from colorless to yellow. However, visual and photometric titrations are impossible if the solution to be analyzed has a strong intrinsic color. Electrometric titration, in particular the so-called dead-stop method, is therefore preferred at the present time. This process is based on a deliberately produced polarization on two identical platinum electrodes. Upon the application of a small potential difference, the voltage arising from the polarization is compensated and the current flow is interrupted. The end point of the titration is indicated by a strong deflection of the galvanometer, which then remains unchanged. This deflection is based on the sharp transition from polarization or depolarization of one electrode to complete depolarization or polarization of both electrodes.

When a ratio of amine to $SO_2$ grater than about 2:1 is used, the mentioned unstable end points occur. When the ratio is less than about 1:1, the excess of sulfur dioxide is no longer bound by the amine and as a result, the solution is unstable and smells pungent.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius and unless otherwise indicated, all parts and percentages are by weight.

EXAMPLE 1

The solvent solution and the titrating agent were prepared by dissolving the particular substances in the corresponding solvent:
(a) Solvent solution
32.0 g of sulfur dioxide (0.5 M) and
149.2 g of triethanolamine (1.0 M) in
1,000 ml of methanol
(b) Titrating agent
50 g of iodine in
1,000 ml of methanol The test substance whose water content was to be determined was dissolved, in an amount depending on the estimated water content, in 20 ml of the solvent solution and titrated to the end point with the titrating agent while stirring continuously and with the exclusion of atmospheric moisture.

EXAMPLE 2

The following Karl-Fischer solutions were prepared
(a) Solvent solution
32.0 g of sulfur dioxide (0.5 M) and
105.1 g of diethanolamine (1.0 M) in
1,000 ml of ethylene glycol monomethyl ether
(b) Titrating agent
50 g of iodine in
1,000 ml of ethylene glycol monomethyl ether The same results were obtained with these solutions as with the solutions of Example 1. The results also remained unchanged after partial or complete replacement of the ethylene glycol monomethyl ether by methanol or propanol.

EXAMPLE 3

The following solutions were used to carry out a coulometric determination of water:
(a) Cathode solution
64.0 g of sulfur dioxide (1.0 M) and
149.2 g of triethanolamine (1.0 M) in
1,000 ml of methanol
(b) Anode solution
analogous, but with the addition of 5 to 10 g of iodine.

The preceding examples can be repeated with similar success by substituting the generically or specifically described reactants and/or operating conditions of this invention for those used in the preceding examples.

From the foregoing description, one skilled in the the art can easily ascertain the essential characteristics of this invention, and without departing from the spirit and scope thereof, can make various changes and modifications of the invention to adapt it to various usages and conditions.

What is claimed is:

1. A solvent solution for use in a Karl-Fischer reagent comprising sulfur dioxide and an amine in a Karl-Fischer reagent solvent, the amine being functionally equivalent to pyridine in a Karl-Fischer reagent, wherein the molar ratio of amine to sulfur dioxide is about 2:1 to 1:1 and the solution is essentially free of pyridine.

2. An essentially pyridine-free Karl-Fischer reagent system for the determination of water comprising (a) a solvent solution containing sulfur dioxide and an amine in a Karl-Fischer reagent solvent, the amine being functionally equivalent to pyridine in a Karl-Fischer reagent, and (b) a titrating agent containing iodine in a Karl-Fischer solvent; the molar ratio of amine to sulfur dioxide being about 2:1 to about 1:1 and the reagent system being essentially free of pyridine.

3. The essentially pyridine-free Karl-Fischer reagent system of claim 2, wherein the solvent is a lower alkanol or a glycol.

4. The essentially pyridine-free Karl-Fischer reagent system of claim 2, wherein the amine is aniline, dimethylaniline or diphenylamine.

5. The essentially pyridine-free Karl-Fischer reagent system of claim 2, wherein the amine is diisopropylamine, tri-n-butylamine or ethylenediamine.

6. The essentially pyridine-free Karl-Fischer reagent system of claim 2, wherein said solvent solution (a) contains only one amine.

7. The essentially pyridine-free Karl-Fischer reagent system of claim 2, wherein the amine is ethanolamine, diethanolamine, triethanolamine, morpholine, N-methylmorpholine, aniline, dimethylaniline, diethylamine, triethylamine, diisopropylamine, tri-n-butylamine, ethylenediamine, or diphenylamine.

8. The essentially pyridine-free Karl-Fischer reagent system of claim 7, wherein the amine is mono-, di- or tri-ethanolamine.

9. The essentially pyridine-free Karl-Fischer reagent system of claim 8, wherein the solvent is methanol.

10. A method for the determination of water in a sample comprising adding the sample to the solvent solution of the Karl-Fischer reagent system of claim 2 to form a mixture and titrating the mixture with the titrating agent of the Karl-Fischer reagent system of claim 2.

11. The method of claim 10, wherein the titrating is carried out with electrometric end point detection.

12. A combination consisting essentially of, in admixture, (a) a solvent solution containing sulfur dioxide and an amine in a Karl-Fischer reagent solvent, the amine being functionally equivalent to pyridine in a Karl-Fischer reagent, and (b) a titrating agent containing iodine in a Karl-Fischer solvent; the molar ratio of amine to sulfur dioxide being about 2:1 to about 1:1 and the combination being essentially free of pyridine.

13. An essentially pyridine-free Karl-Fischer reagent system for the determination of water containing essentially of (a) a solvent solution containing sulfur dioxide and an amine in a Karl-Fischer reagent solvent, the amine being functionally equivalent to pyridine in a Karl-Fischer reagent, and (b) a titrating agent containing iodine in a Karl-Fischer solvent; the molar ratio of amine to sulfur dioxide being about 2:1 to about 1:1 and the reagent system being essentially free of pyridine.

14. A method for the determination of water in a sample consisting essentially of adding the sample to the solvent solution of the Karl-Fischer reagent system of claim 13 to form a mixture and titrating the mixture with the titrating agent of the Karl-Fischer reagent system of claim 13.

* * * * *